United States Patent [19]

Vasilow et al.

[11] Patent Number: 5,073,405
[45] Date of Patent: Dec. 17, 1991

[54] APPLYING A TAPERED ELECTRODE ON A POROUS CERAMIC SUPPORT TUBE BY MASKING A BAND INSIDE THE TUBE AND DRAWING IN ELECTRODE MATERIAL FROM THE OUTSIDE OF THE TUBE BY SUCTION

[75] Inventors: Theodore R. Vasilow, Penn Township, Westmoreland County; Gregory E. Zymboly, Murrysville, both of Pa.

[73] Assignee: Westinghouse Electric Corp., Pittsburgh, Pa.

[21] Appl. No.: 641,390

[22] Filed: Jan. 15, 1991

[51] Int. Cl.$^5$ .............................................. B05D 5/12
[52] U.S. Cl. ................................. 427/105; 427/115; 427/181; 427/203; 427/238; 427/282; 427/287; 427/376.3; 427/294
[58] Field of Search ............... 427/105, 115, 181, 203, 427/238, 282, 287, 376.3, 294

[56] References Cited

U.S. PATENT DOCUMENTS

| 2,730,462 | 1/1956 | Ewing | 117/95 |
| 3,028,266 | 4/1962 | Larsh | 117/232 |
| 4,395,468 | 7/1983 | Isenberg | 429/31 |
| 4,414,337 | 11/1983 | Ichikawa et al. | 501/103 |
| 4,490,444 | 12/1984 | Isenberg | 429/31 |

*Primary Examiner*—Shrive Beck
*Assistant Examiner*—Benjamin L. Utech
*Attorney, Agent, or Firm*—Daniel P. Cillo

[57] ABSTRACT

An electrode is deposited on a support by providing a porous ceramic support tube (10) having an open end (14) and closed end (16); masking at least one circumferential interior band (18 and 18') inside the tube; evacuating air from the tube by an evacuation system (30), to provide a permeability gradient between the masked part (18 and 18') and unmasked part (20) of the tube; applying a liquid dispersion of solid electrode particles to the outside surface of the support tube, where liquid flows through the wall, forming a uniform coating (42) over the unmasked support part (20) and a tapered coating over the masked part (18 and 18').

13 Claims, 1 Drawing Sheet

APPLYING A TAPERED ELECTRODE ON A POROUS CERAMIC SUPPORT TUBE BY MASKING A BAND INSIDE THE TUBE AND DRAWING IN ELECTRODE MATERIAL FROM THE OUTSIDE OF THE TUBE BY SUCTION

The Government of the United States of America has rights in this invention pursuant to Contract No. DE-AC21-80ET-17089, awarded by the United States Department of Energy.

BACKGROUND OF THE INVENTION

This invention relates to masking a portion of the inner surface of a tubular, porous fuel cell support tube during vacuum deposition of an exterior electrode, to provide a taper on the end of the deposited exterior electrode near an end of the support tube.

Solid oxide electrolyte, high temperature, tubular fuel cells, and fuel cell generators employing such cells are well known, and taught by U.S. Pat. Nos. 4,490,444 and 4,395,468, respectively (both Isenberg). The cell contains a porous ceramic support tube of, for example, calcia stabilized zirconia, having an open and a closed end, covered in succession by: a thin film porous air electrode of, for example, doped $LaMnO_3$, applied by aqueous vacuum slurry deposition and sintering; solid oxide electrolyte of, for example, yttria stabilized zirconia, covering most of the air electrode; and porous cermet fuel electrode covering the electrolyte.

Air electrode deposits can be made to cover the entire tube including the closed end, exclusive of about 7.6 cm near the open end; or the middle portion of the tube exclusive of about 2.5 cm near the closed end and about 7.6 cm near the open end, although these dimensions are not critical in any way. This deposition can be accomplished by appropriately coating a selected portion of both the inside and the outside of the tube with a masking material which will vaporize at over about 900° C. Dipping the closed end of a tube into a solution of cellulose acetate is one possibility, to provide a masking film after drying. A vacuum would then be drawn on the inside of the support tube after submerging it in an aqueous slurry of finely divided air electrode powder.

The masking film is impermeable to the water and vacuum, therefore no air electrode powder is deposited in the masked areas. However, the deposit forms at the edge of the masking in an abrupt fashion, and may even grow over the edge of the masking, forming an angle of greater than 90° with respect to the tube center surface. When this type of deposit is sintered, the porous support tubes, especially "thin-wall" porous support tubes (1.0 mm to 1.4 mm wall thickness) can break easily at the sharp joint between the tube and air electrode. Bending stress as low as 50.7 kg/cm$^2$ (719 psi) up to 444.2 kg/cm$^2$ (6,300 psi) have been measured on tubes with sintered air electrodes made by this process. Some tubes are broken simply by handling. The ragged edges can be machined to a taper after air electrode sintering, but such machining is time consuming, causes dust, and can cause tube fracture itself.

General immersion vacuum impregnation of unmasked porous tube walls is taught in Ewing U.S. Pat. No. 2,730,462, where a porous, closed ended tube is immersed in impregnant, air is evacuated from the tube interior and wall surfaces, and one end of the tube is opened to admit impregnant and fill the tube. More Larsh U.S. Pat. No. 3,028,266, where an inflatable, rubber like air bag is placed at the mouth of and along the complete length of slots in stator windings, to prevent resin contact at the mouth of the slots during wire varnish vacuum impregnation. Neither of these methods address the problems of support tube masking to provide exterior, smooth edge electrode coatings after vacuum impregnation.

There has been a long felt need for a simple, inexpensive method to properly mask application of electrode material on a support tube and eliminate abrupt and ragged edges of the electrode ends which lowers bending stress and creates handling problems.

A main object of this invention will be to provide such a method.

SUMMARY OF THE INVENTION

Accordingly, the invention resides in a method of depositing a tapered electrode on a support tube characterized by the steps: (1) providing a ceramic support tube, having a porous wall and two ends, (2) masking at least one circumferential band inside of the tube, where at least the inside of one end of the tube is masked, leaving at least one unmasked band inside of the tube, (3) evacuating air from inside of the tube, to provide a permeability gradation in the tube wall between masked and unmasked circumferential bands, (4) applying a liquid dispersion of solid electrode material particles to the outside surface of the evacuated tube, wherein liquid flows through the support tube wall, the particles coat a uniform deposit thickness on the outside surface over the unmasked inner bands of the tube where there is unrestricted liquid flow, and coat a tapered deposit thickness on the outside surface over at least part of the masked inner bands of the tube where there is restricted liquid flow, with the thinnest part of the taper near the ends of the support tube, and (5) sintering the applied deposit on the support tube.

Preferably, one end of the tube is closed, the inside masked portion is at the closed tube end, and the masking in step (2) utilizes a flexible, inflatable, expanded bladder which sealingly engages the desired circumferential segment of the inside of the tube when inflated. Preferably, the support tube will comprise stabilized zirconia, and the dispersion will comprise doped $LaMnO_3$ particles, having a particle size range from 0.2 micrometer to 75 micrometers, dispersed in water. Water entering the evacuated support tube over a circumferential masking band will have restricted passage and will deposit less particles than water entering over an unmasked band which allows unrestricted flow.

This method solves machining, dust, and breakage problems, by taking advantage of the natural spreading angle in the permeability of the tube. This method also prevents breakage due to low strength at the joint between the tube and air electrode.

BRIEF DESCRIPTION OF THE DRAWING

In order that the invention can be more clearly understood, conventional embodiments thereof will now be described, by way of example, with reference to the accompanying drawings, in which.

DESCRIPTION OF THE PREFERRED EMBODIMENTS

Figure 1:
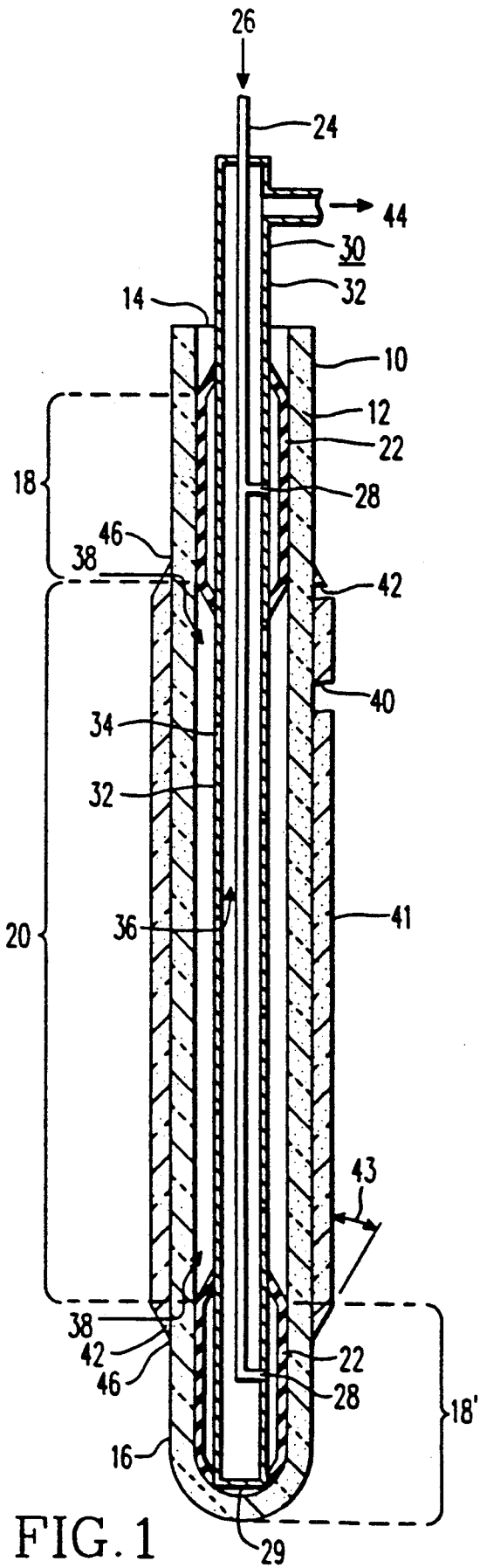
FIG. 1 is a side view in section of one embodiment of a support tube, having inserted therein an inflated bladder which sealingly masks two circumferential bands or segments inside the tube, to provide a permeability gradient in the tube wall between masked and unmasked segments of the tube, in accordance with the method of this invention.

Referring now to FIG. 1, ceramic support tube 10 is shown, having a porous wall 12 usually from 0.8 mm to 2 mm. thick, with an open end 14 and a closed end 16. The tube can also have two open ends. These tubes can be from approximately 20% porous (80% of theoretical density) to 40% porous (60% of theoretical density), with an average pore size, usually of from 1 micrometer to 3 micrometers. They are usually extruded and then sintered. Preferably, these tubes are made of stabilized zirconia, most preferably calcia stabilized zirconia, for example $(ZrO_2)_{.85}(CaO)_{.15}$. They can be made according to the teachings of Ishikawa U.S. Pat. No. 4,414,337, herein incorporated by reference. The closed end of the support tube, when used, can be a solid piece, a plugged sintered piece, or a cemented sintered piece. A solid piece is shown in FIG. 1.

In the method of this invention, such a support tube is interiorly masked near the open end of the tube and preferably also interiorly masked near the other, usually closed end of the tube. The masking will cover at least one and preferably two circumferential bands, segments, or areas 18 and 18' within the tube on the interior tube surface, where at least the inside of the closed end is masked as shown, that is masked similarly to that shown to provide a substantial masked area such as 18'. There will also be an unmasked band, segment, or area 20 inside of the tube. The masking 22 can most simply, be a film layer or deposit of an organic masking material (not shown) which will vaporize or burn off at temperatures below 900° C., during subsequent electrode sintering at up to 1,500° C. Useful organic materials would include cellulose acetate, polyvinyl acetate, polyvinyl butyral, methyl methacrylate, wax emulsions, and the like. This masking film would have a thickness effective to provide a relatively, non-porous seal or barrier to air or liquid such as water, preferably from 0.07 mm. to 0.3 mm. and would sealingly engage the circumferential area 18 inside the support tube 10.

Most preferably, the masking will be in the form of a flexible, expansible, inflatable bladder, mold or balloon, as shown in FIG. 1 as 22 in inflated form. Also shown is very thin capillary tubing 24. A gas 26 such as air is fed through the capillary tubing and through holes or ports 28 disposed along the capillary tubing length, and then into the bladder, as shown, leading to the bladder cavity. The gas pressure forces the bladder to expand and to sealingly engage the circumferential area 18 inside the support tube 10, forming a tight, relatively non-porous seal or barrier to air or liquid such as water. Other means than that shown can be used to inflate the bladders. Where the inside closed end of the support is rounded as shown in FIG. 1 and where a space might be provided between the bladder and the tube, as at point 19, the entire interior closed end is considered masked.

It is also possible that the bladders could be pre-inflated to a thickness in excess of the inside diameter of the support tube and then forced into the tube to form circumferential band masking. The bladder will most preferably be made of a suitable rubber, such as a neoprene rubber, or a flexible plastic material. One advantage of the bladder system of masking, is that it can be a permanent part of the vacuum system 30, joined to and fitting around it at each end as shown in FIG. 1, and would eliminate concerns of completely burning off an interior masking film.

Once the masking is in place, whether a fugitive film or an inflated bladder, or the like, air is evacuated from the inside of the support tube 10 by a vacuum system 30, which can contain an air or water, withdrawal tube 32, made for example of stainless steel, containing holes 34 therethrough along its length, preferable along its middle section. The withdrawal or exhaust tube 32 is disposed within the support tube 10 from the closed end to the open end and can be sealed in place by the masking 22 as shown or by some other means.

Air and water will be free to easily pass through the wall 12 and into the porous support tube 10 within the unmasked band segment, or area 20. However, passage of air or water through the wall 12 over the masking, within the masked band, segment or areas 18 will be slower and somewhat restricted, creating a permeability or flow gradation in the tube wall between masked and unmasked circumferential bends. Thus, air or water can be sucked directly through the wall and into the vacuum system through holes 34 in the air withdrawal tube 32 as shown By unrestricted air or water flow arrow 36 which flow can pass through the support wall perpendicular to the wall surface. Even though the wall is only up to 40% porous, such perpendicular flow is herein considered "unrestricted".

Figure 2:
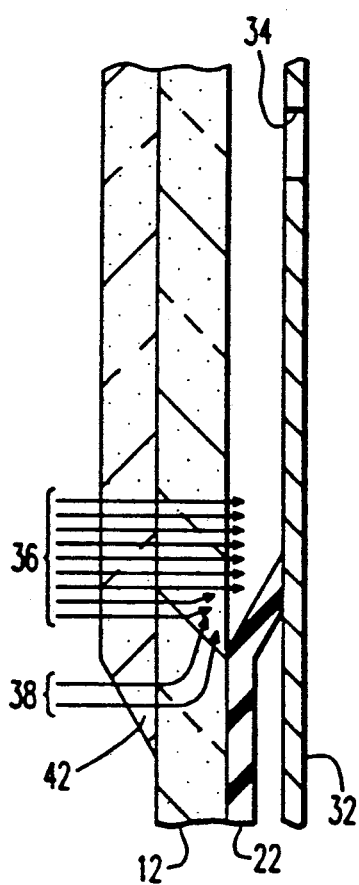
FIG. 2 is a more detailed side view of the tapered deposit on the support tube.

However, air or water entering the support tube wall in the wall band over the circumferential masking bands 18 and 18', shown by restricted air or water flow arrow 38 will have restricted passage, and have to travel substantially parallel to the wall surface, as shown most clearly in FIG. 2, in order to enter the air withdrawal tube, since the masking is non-porous and the vacuum has to draw air or water from within the unmasked circumferential band 20. Thus, when a dispersion of electrode material particles is applied to the outside surface of the evacuated support tube, the dispersion will adhere, impregnate to a minor extent and coat a uniform deposit thickness 40 of electrode material 41 on the outside surface over the unmasked inner band 20. The particles in the dispersion will adhere and coat to a much lesser extent on the outside surface over the masked inner bands 18 and 18', especially at the farthest extent of the masking near the open and closed ends of the support tube. This permeability or flow gradation or difference in flow rate is shown by the number of unrestricted flow arrows 36 versus the number of restricted flow arrows in FIG. 2.

Thus, the particles in the dispersion will coat a tapered deposit thickness 42 over the masked inner bands of the tube, with the thinnest part of the taper near the ends of the support tube, as shown. The taper angle 43 will usually be between 10° to 40°. Since an equal amount of water from the dispersion will contain a certain amount of electrode powder, the position of the support tube through which more water can be drawn inside the tube, will have a thicker deposit of powder on its surface. Thus, since less water from the dispersion will be drawn through the wall over the masked portion 18 of the support tube, less coating will occur over the masked portion until a point is reached furthest away from the unmasked portion 20 of the tube, as at point 46, where no coating will occur.

By having this taper automatically form, no machining is necessary to previously ragged edges at the taper point. This permeability or flow gradation can be shown in FIG. 2 as the difference in ease of movement of water through the support tube wall between bands 18, 18' and 20, for example between air or water flow arrows 36 and 38. It is undesirable to place masking on the outside of the support tube along the length where coating might adhere.

Usually, the entire support tube 10 with attached vacuum system 30 and masking 22 will be dipped in a suspension of finely divided electrode powder and water, and then air and water in the tube will be evacuated as stream 44. The electrode powder will most preferably be an electrode powder which will function as an air electrode of a solid oxide electrolyte fuel cell. Useful powders include doped and undoped oxides or mixtures of oxides in the perovskite family, such as $LaMnO_3$, $CaMnO_3$, $LaNiO_3$, $LaCoO_3$, $LaCrO_3$, and $InO_3$. Preferably, the powder is doped $LaMnO_3$, most preferably strontium doped $LaMnO_3$, for example $La_{.9}Sr_{.1}MnO_3$, which may optionally have some $ZrO_2$ powder added. The powder particle size range is from 0.2 micrometer to 75 micrometers, preferably from 0.75 micrometer to 45 micrometers. Over 75 micrometers diameter the particles in the dispersion will not adhere well and may block pores in the support cell wall; under 0.2 micrometer and porosity suffers due to clogging the pores of the support, which are usually up to 3 micrometers diameter.

Preferably, before the electrode particles are mixed to form a dispersion, they are ball milled in water to reduce agglomeration and insure thorough wetting. The dispersion itself will contain from 1 wt. % solids to 20 wt. % solids, preferably from 2 wt. % solids to 5 wt. %. solids. Under 1 wt. % solids, coating will tend to be uneffective; over 20 wt. % solids it will be difficult to draw water through the support tube wall. The slurry pH at this time will preferably range from 5.5 to 7.5. Carbon dioxide from the air will tend to lower the pH to the range where acidity can start to dissolve some components of the electrode powder, particularly strontium. Therefore, a minor amount of base, such as ammonium hydroxide can be added to maintain a constant pH of from 7 to 8.5. The support tube and vacuum system can be placed vertical or horizontal in the dispersion, although horizontal placement is usually preferred.

After support tube and vacuum system immersion, a low vacuum is drawn, about 550 mm. Hg to 675 mm. Hg to coat the tube. Then, the support tube with its deposit of electrode material is taken out of the dispersion while continuing the vacuum, until the deposit is a damp cake where the particles are held together primarily by surface tension effects. The vacuum is then preferably continued and the coated deposit on the tube is heated in an oven at approximately 90° C. to 120° C. for a time effective to thoroughly dry the deposit. At this point, the deposit is adherent but not tightly bound to the tube. The tube with its coating is then sintered at approximately 900° C. to 1,500° C. to firmly bond the deposit to the tube. Finally, the consolidated, unitary body is cooled. This sintering step will also pyrolize any interior masking, for example cellulose acetate, if such is used.

At this point an electrode covers the support tube. Solid oxide electrode, such as stabilized zirconia, for example yttria stabilized zirconia, can be applied over most of the electrode surface by well known vapor deposition techniques, followed by application of a cermet outer electrode, such as nickel particles in a zirconia skeleton by well known vapor deposition or sintering techniques, to provide a solid oxide fuel cell. Such a cell, to be complete, would also require an axial layer of interconnection material down the tube. The interconnection material can be doped lanthanum chromite as is well known in the art. A series of cells can then be connected to provide a generator.

The invention will now be illustrated with reference to the following non-limiting Example.

EXAMPLE

An extruded ceramic tube, 66 cm. long and 1.2 mm. thick, with an outside diameter of 13 mm., made of calcia stabilized zirconia, having a porosity of 35% ± 3% and an average pore size between 1 micrometer to 2 micrometers was used as a support tube. The support tube had an open end and a rounded closed end. An expandable bladder masking device, attached to each end of a vacuum system, was inserted inside the support tube. The bladder masking device was similar to that shown in FIG. 1. The bladder was in hollow hose form, and fit around a 0.63 cm. (0.25 inch) outside diameter vacuum exhaust or withdrawal tube, made of stainless steel and having slots through its wall, measuring 0.15 cm. wide and 0.32 cm. long, along the middle portion of its length.

The bladder was tightly bound to the exhaust tube by fine stainless steel wire and rubber cement and positioned near the opening and the end of the support tube, as shown in FIG. 1. A fine, hypodermic, stainless steel capillary tube, about 0.5 mm. outside diameter, to be used to inflate the bladders were placed within the exhaust tube and was welded to a drilled opening through the exhaust tube leading to the bladder chamber. Air was pumped into the bladder through the capillary tube so that the bladder sealingly engaged two circumferential bands each about 2.5 cm. long at either end of the support tube, as shown in FIG. 1, forming maskings on the inside of the support tube.

This apparatus was then placed vertically in a room temperature dispersion of water and $La_{.9}Sr_{.1}MnO_3$ particles having diameters from 0.75 micrometer to 30 micrometers, which had previously been ball milled in water to reduce agglomerations. The solids content of the dispersion was 3 weight %. A low vacuum was drawn on the support tube to evacuate air from inside the tube. The water in the dispersion was drawn through the support tube walls and a deposit of $La_{.9}Sr_{.1}MnO_3$ particles was coated on the support tube. The coating was of uniform thickness along the tube between the bladders, over the unmasked inner support tube band. Over the bladders, due to less water flow through that portion of the masked tube, the coating formed a tapered deposit, as shown in the Drawing. The support tube was left immersed in the aqueous dispersion for about 6 minutes to 8 minutes and then taken out of the dispersion. Vacuum was continued outside of the dispersion for about 10 minutes, providing a damp cake of particles about 2 mm. thick in the center of the support tube and tapering off at a low angle at each end of the support tube.

The applied deposit on the support tube was then dried at 110° C. for 1 hour, and finally sintered at 1,400° C., to provide a unitary, bonded air electrode on the support tube. After cooling, the air electrode angle was inspected by microscope and was between 10° and 20°. There was no ragged edge and no sanding was needed to provide a smooth surface. The tube with deposited air electrode was then placed on a wedge located at a position near the open end where the taper stopped. At a distance of 7.6 cm. from the end of the taper, toward the open end of the tube, pressure was applied until the tube snapped at the taper point. A bending stress of 518.6 kg/cm$^2$ (7,356 psi) was required to fracture the tube (17.2 lb. load over a 7.6 cm. span in single cantilever bending). This was superior to the from 50.7 kg/cm$^2$ (719 psi) to 444.2 kg/cm$^2$ (6,300 psi) values measured from the bending stress at the point between air electrode and support when overlapping inside/outside masking was used.

We claim:

1. A method of depositing a tapered electrode on a support tube comprising the steps:
   (1) providing a ceramic support tube, having a porous wall and two ends;
   (2) masking at least one circumferential band inside of the tube, where at least the inside of one end of the tube is masked, leaving at least one unmasked band inside of the tube;
   (3) evacuating air from inside of the tube, to provide a permeability gradation in the tube wall between masked and unmasked circumferential bands;
   (4) applying a liquid dispersion of solid electrode material particles to the outside surface of the evacuated tube, wherein liquid flows through the support tube wall, the particles coat a uniform deposit thickness on the outside surface over the unmasked inner bands of the tube where there is unrestricted liquid flow, and coat a tapered deposit thickness on the outside surface over at least part of the masked inner bands of the tube where there is restricted liquid flow, with the thinnest part of the taper near the ends of the support tube; and
   (5) sintering the applied deposit on the support tube.

2. The method of claim 1, where the support tube comprises stabilized zirconia, the electrode particles comprise doped LaMnO$_3$ having a particle size of from 0.2 micrometer to 75 micrometers, and the dispersion is applied in step (4) by immersing the tube in the dispersion.

3. The method of claim 1, where the support tube has one closed end, is from 20% porous to 40% porous with an average pore size of from 1 micrometer to 3 micrometers, the electrode particles are ball milled with water and then added to water to form the dispersion, and where the inside masking in step (2) is near the closed end.

4. The method of claim 1, where the dispersion has a pH of from 7 to 8.5, and comprises from 1 wt. % to 20 wt. % electrode particle solids.

5. The method of claim 1, where the masking in step (2) is by applying to the circumferential band to be masked, a film of organic material which will burn off at temperatures below 900° C.

6. The method of claim 1, where the masking in step (2) is by sealingly engaging an inflated bladder to the circumferential band to be masked.

7. The method of claim 1, where the electrode particles are dispersed in water, and in step (4), liquid entering the evacuated support tube over the circumferential masking band will have restricted passage and travel substantially parallel to the support wall surface in order to flow through the porous support wall and will deposit less particles than liquid entering over the unmasked band which allows unrestricted flow.

8. The method of claim 1, including as final steps, application of a solid oxide electrolyte over most of the electrode deposit and then applying an outer cermet electrode over the electrolyte.

9. A support tube having a tapered electrode applied by the method of claim 1.

10. A method of depositing a tapered electrode on a support tube comprising the steps:
    (1) providing a stabilized zirconia support tube, having a 20% porous to 40% porous wall, an open end and a closed end;
    (2) masking at least one circumferential band inside of the tube, where at least the inside of the closed end is masked, by sealingly engaging an inflated bladder to the circumferential band to be masked, leaving at least one unmasked band inside of the tube;
    (3) evacuating air from inside of the tube, to provide a permeability gradation in the tube wall between masked and unmasked circumferential bands;
    (4) applying an aqueous dispersion of solid, doped LaMnO$_3$ particles to the outside surface of the evacuated tube by immersing the tube in the dispersion, wherein water flows through the support tube wall, the particles coat a uniform deposit thickness on the outside surface over the unmasked inner bands of the tube where there is unrestricted liquid flow, and coat a tapered deposit thickness on the outside surface over at least part of the masked inner bands of the tube where there is restricted liquid flow, with the thinnest part of the taper near the ends of the support tube; and
    (5) sintering the applied deposit on the support tube.

11. The method of claim 10, where the support tube has an average pore size of from 1 micrometer to 3 micrometers, the doped LaMnO$_3$ particles have a particle size from 0.2 micrometer to 75 micrometers, the dispersion has a pH of from 7 to 8.5, and the dispersion comprises from 1 wt. % to 20 wt. % solids 12. The method of claim 10, where in step (4), water entering the evacuated support tube over the circumferential masking band will have restricted passage and travel substantially parallel to the support wall surface in order to flow through the porous support wall and will deposit less particles than water entering over the unmasked band which allows unrestricted flow.

13. The method of claim 10, including as final steps, application of a solid oxide electrolyte over most of the electrode deposit and then applying an outer cermet electrode over the electrolyte.

* * * * *